United States Patent
Corwin et al.

(10) Patent No.: US 8,673,643 B2
(45) Date of Patent: Mar. 18, 2014

(54) CLOSED LOOP MONITORING OF AUTOMATED MOLECULAR PATHOLOGY SYSTEM

(75) Inventors: Alex David Corwin, Niskayuna, NY (US); Robert John Filkins, Niskayuna, NY (US); Jun Xie, Niskayuna, NY (US); Christopher James Sevinsky, Watervliet, NY (US); Kashan Ali Shaikh, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 458 days.

(21) Appl. No.: 12/957,203

(22) Filed: Nov. 30, 2010

(65) Prior Publication Data

US 2012/0135458 A1    May 31, 2012

(51) Int. Cl.
*G01N 35/02* (2006.01)
*G01N 33/53* (2006.01)
*B05D 3/00* (2006.01)
*G01N 1/31* (2006.01)
*G01N 1/30* (2006.01)
*G01N 33/48* (2006.01)

(52) U.S. Cl.
USPC ............ 436/50; 427/2.13; 435/40.5; 436/800

(58) Field of Classification Search
USPC ........................................ 435/40.5; 427/2.13
See application file for complete search history.

(56) References Cited

U.S. PATENT DOCUMENTS

| | | | |
|---|---|---|---|
| 4,741,043 A | 4/1988 | Bacus | |
| 5,830,413 A | 11/1998 | Lang et al. | |
| 6,215,892 B1 | 4/2001 | Douglass et al. | |
| 7,226,788 B2 | 6/2007 | Torre-Bueno | |
| 2005/0032129 A1 | 2/2005 | Hasui | |
| 2008/0212866 A1 | 9/2008 | Lett et al. | |
| 2009/0253163 A1 | 10/2009 | Xie et al. | |
| 2010/0240021 A1 | 9/2010 | Berndt | |

FOREIGN PATENT DOCUMENTS

| | | |
|---|---|---|
| EP | 0843169 A1 | 5/1998 |
| WO | 2003045560 A2 | 6/2003 |
| WO | 2003106157 A2 | 12/2003 |
| WO | WO 03/106157 * | 12/2003 |
| WO | 2008109422 A1 | 9/2008 |

OTHER PUBLICATIONS

Huisman et al. "A Restaining Method to Restore Faded Fluorescence in Tissue Specimens for Quantitative Confocal Microscopy" Cytometry Part A 71A: 875-881, 2007.*
Lognin et al. "Comparison of anti-fading agents used in fluorescence microscopy: image analysis and laser confocal microscopy study" J Histochem Cytochem 1993 41: 1833-1840.*
Olympus I "Olympus FluoView Resource Center: Fluorophores for Confocal Microscopy" 16 pgs copyright 2004-2009.*
Olympus II "Olympus FluoView Resource Center: Specimen Preparation" 6 pgs copyright 2004-2009.*
Song et al. "Photobleaching Kinetics of Fluorescein in Quantitative Fluorescence Microscopy" Biophysical Journal vol. 68 Jun. 1995 2588-2600.*
Ingmar et al.; "Development of Fast Automated Staining Procedures using Phastsystem", Electrophoresis; vol. 9, Issue 1, Abstract-1Page. 1988.
Robert et al.; "A Fluorescence Digital Image Microscopy System for Quantifying Relative Cell Numbers in Tissue Culture Plates", Cytometry; vol. 24, Issue 3, Jul. 1, 1996; Abstract-1Page.
Search Report and Written Opinion from corresponding PCT Application No. PCT/EP2011/071241 dated Feb. 13, 2012. 19 pgs.

* cited by examiner

*Primary Examiner* — Thane Underdahl
(74) *Attorney, Agent, or Firm* — Jenifer Haeckl

(57) ABSTRACT

A closed loop automated method for staining of a biological sample is provided. The method comprises providing a biological sample, staining at least a portion of the biological sample by flowing in a reagent, monitoring one or more optical characteristics of the biological sample, and calculating a figure of merit based on at least one of the optical characteristics. An automated device for iterative staining of a biological sample is also provided.

17 Claims, 2 Drawing Sheets

CLOSED LOOP MONITORING OF AUTOMATED MOLECULAR PATHOLOGY SYSTEM

BACKGROUND

Figure 1:
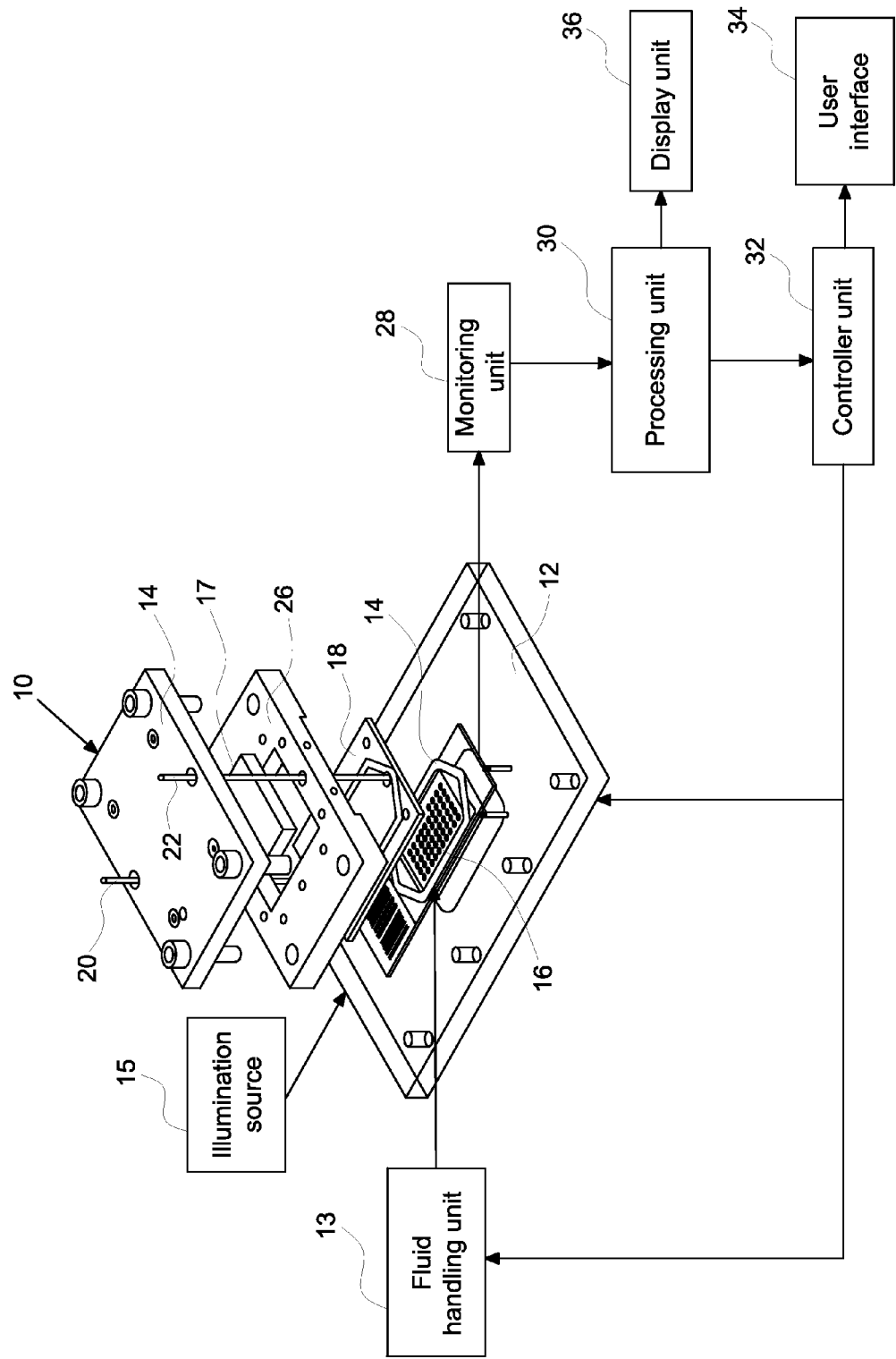

The invention relates generally to automated methods and devices for iterative staining of biological samples for imaging applications.

Biological samples are used for analytic and diagnostic purposes, such as diagnosing diseased tissue at a molecular level. A biological sample, such as tissue micro arrays (TMA), on which tissue samples are fixed are typically stained with a morphological stain or biomarker. The stained TMA are then analyzed manually with a microscope, or an image may be taken of the TMA for subsequent analysis or comparison. After the first stain is applied and imaged, one or more serial or successive stains or biomarkers may be applied and the TMA may be analyzed again. The two or more serial images may then be compared. A single staining cycle may comprise the steps of flowing a stain (antibody) over the tissue, incubating the stain for an appropriate time, rinsing away the stain to reduce background fluorescence, imaging the slide, and bleaching away the stain. As part of the multiplexing technique developed for fluorescent imaging, sequential staining, rinsing, and destaining cycles are required. The staining cycle may be then repeated for multiple stains. For multiplexed applications, the TMA needs to be stained with multiple molecular probes to investigate protein expression or spatial distribution quantitatively or qualitatively.

The staining process is typically performed using time-consuming manual techniques that are susceptible to error. Thus, the total operation time is the sum of each of these steps multiplied by the total number of applied stains. Currently, time for each step is determined based on the amount of fluids required for each step. The time for each step is fixed independent of which antibody (stain) is being applied. Thus a very weak stain will be subjected to the same bleaching time as a much stronger stain, even though a shorter bleaching time may suffice. The reagents used in the staining process are often expensive and have limited shelf life thereby requiring special handling techniques Therefore, it is desirable to provide a method for optimizing one or more steps in a staining cycle. It is also desirable to automate the process and reduce manual intervention to make the process time efficient and reliable.

BRIEF DESCRIPTION

In one embodiment, an automated device for iterative staining of a biological sample is provided. The automated device comprises a flow cell in fluid communication with a staining agent unit and a bleaching agent unit, wherein the flow cell comprises a surface configured to operatively engage the sample therewith, an illumination source for illuminating at least a portion of the biological sample, a monitoring unit operatively coupled to the flow cell and configured for monitoring one or more optical characteristics of the biological sample before, during, and/or after the application of at least one of a staining agent and a destaining agent. The device further comprises a processing unit for determining a figure of merit based on at least one of the optical characteristics of the biological sample, and a controller unit in communication with the processing unit and the flow cell, wherein the controller unit is configured to control the application of at least one of the staining agent and the destaining agent based at least in part on the figure of merit.

In another embodiment, a closed loop automated method for staining of a biological sample is provided. The method comprises providing a biological sample, staining at least a portion of the biological sample by flowing in a reagent, monitoring one or more optical characteristics of the biological sample, and calculating a figure of merit based on at least one of the optical characteristics.

DRAWINGS

Figure 2:
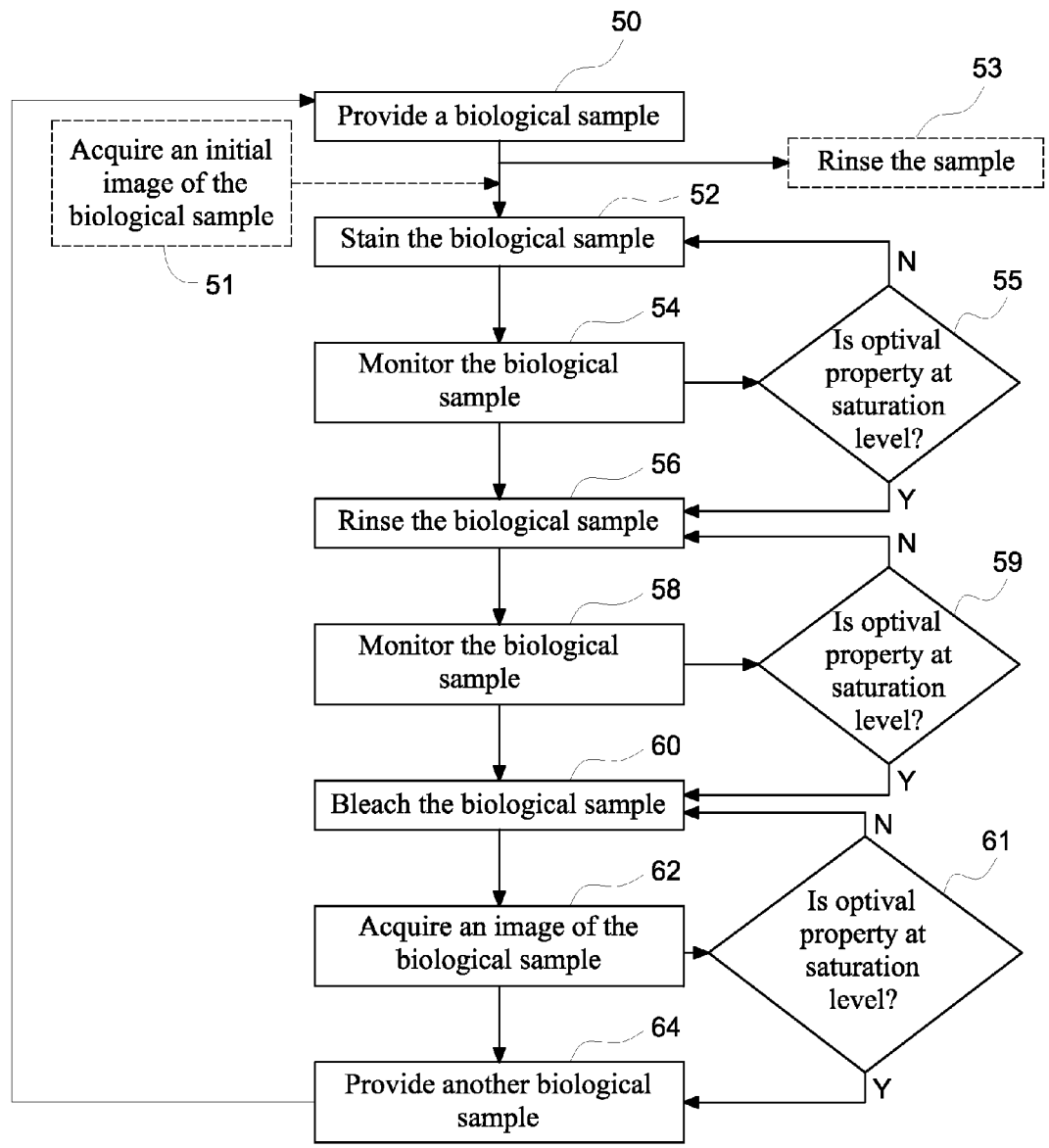

These and other features, aspects, and advantages of the present invention will become better understood when the following detailed description is read with reference to the accompanying drawings in which like characters represent like parts throughout the drawings, wherein:

FIG. 1 is a schematic view of an example of a closed loop automated system of the invention; and FIG. 2 is a flow chart for example steps of a method for closed loop monitoring of molecular pathology systems.

DETAILED DESCRIPTION

Embodiments relate to methods and systems for closed loop monitoring of an automated molecular pathology system for molecular imaging. The methods and systems enable optimized operation in molecular imaging. In certain embodiments, the automated molecular pathology system may operate with minimal operator intervention by reducing or eliminating the need to transfer samples (e.g., tissue samples on a slide within the flow cell). The systems and methods may reduce or eliminate the need to displace samples between the staining component and the imaging component. Closed loop monitoring minimizes both reagent volume and reagent dwell time within the system thereby saving on expensive reagents, such as fluorescence labeled antibodies, and minimizing reagent decomposition or side reactions.

In certain embodiments, a closed loop automated method for staining a biological sample comprises providing a biological sample, staining at least a portion of the biological sample, monitoring one or more optical characteristics of the biological sample during staining, and determining a figure of merit based on at least one of the optical characteristics. The method may further comprises rinsing at least a portion of the biological sample, monitoring one or more optical characteristics from the portion of the biological sample during rinsing, and determining a figure of merit based on at least one of the optical characteristics. The method may also comprise destaining at least a portion of the biological sample, monitoring one or more optical characteristics from the portion of the biological sample during destaining, and determining a figure of merit based on at least one of the optical characteristics. The biological sample may be incubated for a determined period of time after being stained to provide sufficient time for the antibodies to bind with the molecules in the biological sample. The imaging for the staining step may be performed during incubation period. In one example, monitoring during one or more of staining, destaining and rinsing comprises acquiring images of the biological sample, and determining the figure of merit comprises determining a light intensity from the portion of the biological sample using the acquired images. Monitoring during rinsing may comprise acquiring images from regions away from the biological sample. For example, the images may be acquired from regions outside the biological sample.

To more clearly and concisely describe the subject matter of the claimed invention, the following definitions are provided for specific terms, which are used in the following description and the appended claims. Throughout the specification, exemplification of specific terms should be considered as non-limiting examples.

As used herein, the term "biological sample" refers to a sample obtained from a biological subject, including sample of biological tissue or fluid origin obtained in vivo or in vitro. Such samples may be, but are not limited to, tissues, fractions, and cells isolated from mammals including, humans.

In some embodiments, the biological sample includes tissue sections of colon, normal breast tissue, prostate cancer, colon adenocarcinoma, breast tissue microarray, breast TMA, or normal prostrate. A tissue section may include a single part or piece of a tissue sample, for example, a thin slice of tissue or cells cut from a tissue sample. In some embodiments, multiple sections of tissue samples may be taken and subjected to analysis, provided the methods disclosed herein may be used for analysis of the same section of the tissue sample with respect to at least two different targets (at morphological or molecular level). In some embodiments, the same section of tissue sample may be analyzed with respect to at least four different targets (at morphological or molecular level). In some embodiments, the same section of tissue sample may be analyzed with respect to greater than four different targets (at morphological or molecular level). In some embodiments, the same section of tissue sample may be analyzed at both morphological and molecular levels. A tissue section, if employed as a biological sample may have a thickness in a range that is less than about 100 microns, in a range that is less than about 50 microns, in a range that is less than about 25 microns, or in range that is less than about 10 microns.

As used herein, the term "probe" refers to an agent including a binder and a signal generator. In some embodiments, the binder and the signal generator of the probe are embodied in a single entity (e.g., a radioactive or fluorescent molecule capable of binding a target). In alternative embodiments, the binder and the signal generator are embodied in discrete entities (e.g., a primary antibody capable of binding target and labeled secondary antibody capable of binding the primary antibody).

As used herein, the term "binder" refers to a biological molecule that may non-covalently bind to one or more targets in the biological sample. A binder may specifically bind to a target. Suitable binders may include one or more of natural or modified peptides, proteins (e.g., antibodies, affibodies, or aptamers), nucleic acids (e.g., polynucleotides, DNA, RNA, or aptamers); polysaccharides (e.g., lectins, sugars), lipids, enzymes, enzyme substrates or inhibitors, ligands, receptors, antigens, haptens, and the like. A suitable binder may be selected depending on the sample to be analyzed and the targets available for detection.

As used herein, the term "signal generator" refers to a molecule capable of providing a detectable signal using one or more detection techniques (e.g., spectrometry, calorimetry, spectroscopy, or visual inspection). Suitable examples of a detectable signal may include an optical signal, and electrical signal, or a radioactive signal. In one example, the signal generator may include a lumiphore or a fluorophore.

As used herein the term "lumiphore" refers to a chemical compound that demonstrates luminescence including chemoluminescence, bioluminescence, phosphorescence, and photoluminescence. Representative examples include, but are not limited to, luminol, lucigenin, acridans, acridinium esters, and dioxetanes, and fluorophores.

As used herein, the term "fluorophore" refers to a chemical compound, which when excited by exposure to a particular wavelength of light, emits light (at a different wavelength. Fluorophores may be described in terms of their emission profile, or "color." Green fluorophores (for example Cy3, FITC, and Oregon Green) may be characterized by their emission at wavelengths generally in the range of 515-540 nanometers. Red fluorophores (for example Texas Red, Cy5, and tetramethylrhodamine) may be characterized by their emission at wavelengths generally in the range of 590-690 nanometers. Examples of fluorophores include, but are not limited to, 4-acetamido-4'-isothiocyanatostilbene-2,2' disulfonic acid, acridine, derivatives of acridine and acridine isothiocyanate, 5-(2'-aminoethyl)amino naphthalene-1-sulfonic acid (EDANS), 4-amino-N-[3-vinylsulfonyl)phenyl] naphthalimide-3,5 disulfonate (Lucifer Yellow VS), N-(4-anilino-1-naphthyl)maleimide, anthranilamide, Brilliant Yellow, coumarin, coumarin derivatives, 7-amino-4-methylcoumarin (AMC, Coumarin 120), 7-amino-trifluoromethylcouluarin (Coumaran 151), cyanosine; 4',6-diaminidino-2-phenylindole (DAPI), 5',5"-dibromopyrogallol-sulfonphthalein (Bromopyrogallol Red), 7-diethylamino-3-(4'-isothiocyanatophenyl)-4-methylcoumarin, -, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), eosin, derivatives of eosin such as eosin isothiocyanate, erythrosine, derivatives of erythrosine such as erythrosine B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein, fluorescein isothiocyanate (FITC), QFITC (XRITC); fluorescamine derivative (fluorescent upon reaction with amines); IR144; IR1446; Malachite Green isothiocyanate; 4-methylumbelliferone; ortho cresolphthalein; nitrotyrosine; pararosaniline; Phenol Red, B-phycoerythrin; o-phthaldialdehyde derivative (fluorescent upon reaction with amines); pyrene and derivatives such as pyrene, pyrene butyrate and succinimidyl 1-pyrene butyrate; Reactive Red 4 (Cibacron® Brilliant Red 3B-A), rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl Rhodamine, tetramethyl rhodamine isothiocyanate (TRITC); riboflavin; rosolic acid and lathanide chelate derivatives, quantum dots, cyanines, and squaraines.

As used herein the term 'oxidant" or "oxidizing agent" refers to a destaining agent that substantially inactivates a lumiphore. In one embodiment, the destaining agent comprises a bleaching reagent. Representative oxidizing agents include active oxygen species, hydroxyl radicals, singlet oxygen, hydrogen peroxide, or ozone such as hydrogen peroxide, potassium permanganate, sodium dichromate, aqueous bromine, iodine-potassium iodide, or t-butyl hydroperoxide.

Multiplexing or multiplexed analysis generally refers to analysis of multiple targets in a biological sample using the same detection mechanism.

In molecular imaging, a signal generator (such as, fluorophore) may be excited and the signal (such as, fluorescence signal) obtained may be observed and recorded in the form of a digital signal (for example, a digitalized image). For multiplexing, a similar procedure may be repeated for the plurality of different signal generators (if present) that are bound in the sample using the appropriate fluorescence filters. In some embodiments, a series of probes may be contacted with the biological sample in a sequential manner to obtain a multiplexed analysis of the biological sample. In some embodiments, a series of probe sets (including at most 4 probes in one set) may be contacted with the biological sample in a sequential manner to obtain a multiplexed analysis of the biological sample.

As used herein, the term "figure of merit" includes, but is not limited to a light intensity, a contrast of image, a Brenner gradient, or a signal to background ratio.

Monitoring may be performed at two or more processing steps in the staining cycle. Each staining cycle may comprise staining at least a portion of the biological sample, rinsing away the stain to reduce background fluorescence, destaining the stain. The staining cycle may be repeated for multiple stains. During staining the sample may be incubated for a determined time period. During one of more steps in the staining cycle, signals generated by corresponding portions of the biological sample or portions away from the biological sample may be used to determine the amount of staining, destaining and/or rinsing. In one example, monitoring comprises imaging. Imaging may be used to obtain signals representative of the amount of staining, destaining and/or rinsing that takes place in the biological sample during a staining cycle. In some embodiments, a monitoring unit may comprises a microscope operatively coupled to a camera. In some embodiments, a user may utilize the monitoring unit to record images in more than one field on the sample slide to locate and map multiple stained entities in the sample. The monitoring unit may be operatively coupled to an image capture window of the flow cell such that a sample is positioned within a field of view of the imaging unit. In one example, the monitoring unit may be disposed adjacent the flow cell. The image capture window may be defined by the substrate (e.g., microscope slide) upon which the sample is disposed. The image capture window may include an optically transmissive material on the underside of the slide-receiving member.

Each of the staining, rinsing and bleaching steps may be accomplished by flowing a solution containing a particular reagent over the biological sample positioned within the flow cell. The following parameters may be controlled to enhance reactivity and, thereby, reduce reagent consumption (1) flow cell internal volume; (2) flow cell internal temperature; (3) timing of mixing of constituent parts of the oxidizing solution (e.g., hydrogen peroxide and sodium bicarbonate); (4) extent of agitation of the solutions as they pass the sample; and (5) bubble removal or degassing of the flow cell. Appropriate regulation of these parameters also may reduce sample degradation, permitting a single sample to yield more data.

Accessory devices, such as heating elements or agitation elements (e.g. an acoustic piezoelectric component) may be operatively coupled to the flow cell. In one example, the accessory devices may be positioned away from the image capture window through which a microscope, coupled to a camera, may capture images of the sample during the various phases of processing.

The disclosed methods may be performed in a system that comprises a flow cell configured to enable enhanced access to the sample through an image capture window. The automated methods for staining a biological sample may be performed by employing the techniques disclosed in U.S. Patent Application Publication No. 2009/0253163 titled "ITERATIVE STAINING OF BIOLOGICAL SAMPLES" which is incorporated herein by reference.

FIG. 1 illustrates a closed loop system for an automated molecular pathology system. The system comprises a flow cell 10 having an enclosed flow chamber positioned above a tissue sample. The flow cell 10 may comprise a solid support-receiving member 12, a gasket 14 with a central opening configured to receive a tissue sample positioned on a slide 16, a lid 18, an inlet port 20, and an outlet port 22. The flow cell 10 defines a closed chamber when a slide 16 is positioned in the slide-receiving member 12 and the gasket 14 is sandwiched between the slide 16 and the lid 18. As the flow chamber is enclosed inside the flow cell 10, fluid evaporation and, consequently, reagent loss is minimized. Also, the closed configuration improves temperature control.

The solid support-receiving member 12 is compatible with a range of chemical and temperature variations. In one embodiment, the slide holder may consist of a base and a pin or tab system for securing the slide in the chamber.

In some embodiments, the flow cell 10 may be fixed on a microscope stage for the monitoring process. This allows the sample to be exposed to a series of reagents without manual intervention thereby eliminating realignment of the sample on the microscope stage for image acquisition or registration. This is particularly useful for multiplexed staining and imaging as images acquired after each staining step may be superimposed to form a composite image. The flow cell 10 may be a modular unit that is adapted to fit onto a microscope stage. Alternatively, the flow cell 10 may be an integrated unit including a microscope stage.

The flow cell 10 may be operatively coupled to a fluid handling unit 13 that may comprise a staining agent unit (not shown) and a destaining agent unit (not shown). In one embodiment, the staining agent unit is configured to apply a plurality of staining agents. The flow cell 10 may further be coupled to an illumination source 15 for illuminating at least a portion of the biological sample disposed in the flow cell 10. Non-limiting examples of the illumination source may include metal halide source, mercury arc lamp, or a light emitting diode. A shutter (not shown) of the illumination source 15 may be shut off when the imaging unit is not acquiring images from the biological sample. Closing the shutter may decrease the amount of photo-bleaching of the biological sample. In case of continuous imaging, the shutter of the illumination source may be kept open throughout the duration of imaging.

The system may further comprise fluidic and temperature control subsystems to control fluidic delivery and solution temperature in the internal chamber of the flow cell 10. In one embodiment, the fluidic control system may further comprise reservoirs, flow sensors, mixing chambers, and degassers to prepare one or more reagents prior to injection into the flow cell. The advantage of such a subsystem is to avoid the need of premixing and storing reagents that may have limited stability or shelf life. The fluidic control subsystem is in fluidic communication with the inlet port 20 and outlet port 22 of the flow.

The premixer, which is positioned upstream of the flow cell 10, may be based on a chamber design or a tube design. The chamber design may include a small vessel with inlet and outlet ports and containing a mechanical mixer. In some embodiments, the solutions are mixed at the molecular level by using a premixer to intersperse the reactants immediately prior to the reagent is introduced into the flow cell 10. Mixing times should be sufficiently long to generate the reagent and sufficiently limited to prevent decomposition.

The gasket 14 may comprise a central opening configured to receive a tissue sample positioned on a slide. The gasket 14 may be made of a deformable, chemically inert, rubber or plastic that retains the liquid applied to the flow chamber. The central opening of the gasket maybe sized to maximize the field of view of the image acquisition window.

The inlet and outlet ports 20 and 22 are preferably placed away from the image acquisition window. Thus, the inlet and outlet ports may be positioned in the gasket 14 or upon the lid 18. The inlet and outlet ports 20 and 22 may be similarly sized so that the in-flow rate and the out-flow rate are coordinated to achieve a desired rate of flow across the sample.

A temperature control unit may comprise a thermoelectric stage 17 for temperature control and a resistance temperature detector or thermistor for temperature measurement. For configurations wherein the bottom surface of the temperature control unit is in direct contact with the fluid, the contacting surface 24 may be made of chemical resistant material, such as stainless steel or titanium. A frame 26 may also be used to position the components of the temperature control unit.

In some embodiments, the invention may further comprise a piezo-electric element connected to the flow chamber and capable of producing vibration within the flow chamber by conversion of low voltage electrical signals into acoustic energy. In a preferred embodiment the piezo-electric element maybe composed of a ceramic, quartz ($SiO_2$) or barium titanate ($BaTiO_3$). The configuration of the piezo-electric element provides ultrasonic agitation and influences the flow profile of reagents through the fluid chamber. This is particularly advantageous wherein the desired staining reaction is diffusion limited and conventional mechanical mixing is prohibited by the flow cell geometry.

The monitoring unit 28 may comprise a photomultiplier tube, or a photodiode, a charge coupling device, a camera and other suitable image-receiving devices. The monitoring unit 28 may comprise a microscope operatively coupled to an image-receiving device, such as but not limited to, a camera. Although not illustrated, the monitoring unit 28 may further comprise optical elements, such as but not limited to, an objective lens. The image-receiving device is capable of recording images of the sample while the sample is disposed between the slide and the flow channel housing. The monitoring unit 28 may also include a positioning device, such as an actuator operatively coupled to the camera and configured for adjusting a position of the camera relative to the flow cell. The positioning device may move objective lens to different fields of interest on the sample, and perform auto-focus operations relative to the sample.

In some embodiments, the monitoring unit 28 may be in communication with a processing unit 30. The processing unit 30 in turn may be in communication with a controller unit 32. In some embodiments, the monitoring unit 28 and/or processing unit 30 may be configured for identifying a saturation in light intensity value during staining, destaining or rinsing steps. Non-limiting examples of the processing unit 30 may include an image processing unit.

The controller unit 32 may be in communication with a control input or user interface (show) 34. The controller unit 32 may be configured for controlling the application of at least one of the staining agent and the decolorizing agent based at least in part on the images generated by the imaging system. The controller unit 32 may control the various components of the flow cell system, including for example the thermal control unit, the premixer, the vibrational unit, and the pumps. Where the flow cell 10 is incorporated into a combined sample processing and image acquisition system, the image acquisition components (e.g., microscope or camera) may also be controlled by a computer.

The processing unit 30 may be configured to analyze the image acquired by the monitoring unit 28. In one example, the monitoring unit 28 may acquire images in real-time. In this example, the image processing unit 30 may process the images in real-time. The processing unit 30 may determine the light intensity or color from the acquired images. In one example, for the staining step, the light intensity may be plotted as a function of time. The controller unit 32 may be intimated when the light intensity reaches a saturation point. In a closed loop system, the controller unit 32 may transmit a signal to the flow cell 10 indicating the flow cell to stop the staining step and to move to the next step, such as the rinsing step. Similarly, for bleaching and rinsing steps, the light intensity may be plotted with respect to time, and as the light intensity value stabilizes or as the rate of change of light intensity reaches below a certain rate the corresponding process (bleaching or rinsing) may be stopped, and the next step in the staining cycle may be started. The rate of change of the light intensity may be pre-fed in the system using the user interface 34. In one embodiment, the actual light intensity values or rate of change of light-intensity values may be compared with the pre-fed values, and if required, the pre-fed values may be updated and co-related to the corresponding biological sample or the signal generator. In some embodiments, the monitoring unit 28 and/or the processing unit 30 may be further configured to determine an exposure time for the sample for one or more steps in the staining cycle.

Automation may be achieved through computer control of one or more of the process steps involved in staining cycle, such as but not limited to, addition of staining reagents and oxidant. Where the flow cell system is incorporated into a combined sample processing and image acquisition system, the image acquisition components (e.g., microscope or camera) may also be controlled by software such as a program written in LabVIEW or C.

In some embodiments, one or more of the observing or correlating steps may be performed using computer-aided means. In embodiments where the signal(s) from the signal generator may be stored in the form of digital image(s), computer-aided analysis of the image(s) may be conducted. In some embodiments, images (e.g., signals from the probe(s) and morphological stains) may be overlaid using computer-aided superimposition to obtain complete information of the biological sample, for example topological and correlation information.

In certain embodiments, a closed loop automated method for staining cycle of a biological sample is provided. The method comprises positioning a biological sample, such as a tissue section on a microscope slide, in a flow cell, applying a fluorescent label or a lumiphore to the sample in a manner to allow sufficient contact time between the lumiphore and the sample which are typically in the range of 30 to 60 minutes depending on the concentration and type of label used, rinsing the biological sample by applying a wash solution, for example an appropriate buffer solution to wash away any unbound fluorescent label or lumiphore, acquiring an image of the labeled sample and determining a saturation in light intensity, and bleaching. Wherein acquiring the signal comprises acquiring the signal through an image acquisition window. Imaging may be performed after one or more of staining, rinsing and bleaching. Alternatively, imaging may be performed after each of staining, rinsing and bleaching. The method further comprises measuring light intensity values of the signal generated and correlating the signal with specific labeling of a biomarker. The imaging may be performed at time intervals that are greater than exposure time of the sample.

The imaging may be carried out continuously throughout the staining cycle, or through a particular step in the staining cycle. In some embodiments, the method comprises real-time monitoring of at least a portion of the tissue along with a real-time determination of whether the desired state has been reached (i.e. how much bleaching/staining/rinsing has occurred). In these embodiments, the images may be continuously acquired images during staining, destaining or rinsing. In other embodiments, the method comprises intermittent monitoring of the biological sample for a particular step in the staining cycle. In these embodiments, the images may be acquired intermittently during staining, destaining or rinsing. For example, imaging may be performed at a constant time interval for the particular step, such as the staining step. Alternatively, the imaging may be carried out at a varying time interval for the particular step, with the time interval decreasing as the time progresses. The images may be acquired at time intervals greater than an exposure time of the biological sample to the illumination source. In case of intermittent imaging, the illumination shutter may be closed when the sample is not being imaged to reduce the amount of photo-bleaching for the sample.

In one embodiment, the imaging may be a bright field imaging. The bright field imaging may enable identification of labels other than the fluorescence imaging. The imaging may be used to collect data corresponding to color and/or light intensity.

Embodiments of the invention refer to monitoring one or more optical characteristics for the one or more steps of the staining cycle. In one embodiment, the light intensity of the fluorescence from the stained samples may be used to determine the time period for carrying out the staining/bleaching or rinsing step.

At step 50, a biological sample is provided. The biological sample is disposed in a flow cell. At step 52, at least a portion of the biological sample is stained. Optionally, at step 51, an initial image may be acquired before staining the sample. Data from the initial image or the background image may be used to normalize intensity data from the subsequent images. Optionally, at step 53, the method may include the step of washing the biological sample solution prior to acquiring the initial image of the sample before staining. For example, after providing the sample (step 50) a substantially colorless washing solution may be introduced into the flow channel or in a space defined between the surface on which the sample is operatively engaged and a slide. The washing solution may be flushed to condition or prime the sample by bringing the sample and the biological entities making up the sample into contact with a liquid. The washing step may also provide a suitable reference to normalize light intensity data.

The various method steps for applying a staining agent, and applying a bleaching agent may be accomplished by a variety of washing and/or fluid application techniques. For example, application of washing solutions, staining agents, and/or decolorizing agents may be accomplished by a variety of known laboratory procedures including, but not limited to pipetting; aspiration; mixing; centrifuging; and combinations of such processes.

In some embodiments, one or more of the steps may be automated and may be performed using automated systems. In some embodiments, all the steps of the staining cycle may be performed using automated systems.

At step 54, the biological sample is monitored with respect to one or more optical characteristics of the biological sample. In one embodiment, monitoring comprises imaging the biological sample. The imaging may be a full field imaging. The biological sample may be imaged to determine an amount of staining for at least a portion of the biological sample. As the imaging progresses the light intensity of the biological sample increases. One or more of the optical characteristics may reach a saturation state. For example, during staining, the light intensity reaches a saturation level when the staining is completed. The imaging may be carried out to determine when the light intensity reaches a saturation level. Subsequent to monitoring, a figure of merit may be calculated based on at least one of the optical characteristics. The figure of merit may be determined after each monitoring step. The figure of merit may be chosen based on the nature of the biological sample, marker or dye. In case of imaging, at step 55, data acquired from the images may be analyzed to determine when the light intensity reaches its saturation level. The step 55 may be performed after each imaging step (step 54). If the light intensity has reached a saturation level, the system may shift to the next step, which is rinsing. At step 56, the method further comprises rinsing at least a portion of the biological sample. At step 58, the sample is monitored, for example, imaged to determine an amount of rinsing for at least a portion of the biological sample. At step 59, data acquired from the images is analyzed to determine the progress in the step of rinsing. If the desired progress has occurred, i.e. the background signal has dropped below some threshold in the case of rinsing, the step of rinsing may be stopped and the next step of the protocol may be started. In this way each operation is given only as much time as required as opposed to a globally specified longer time required to work for all cases. In one embodiment, during rinsing, the imaging may be performed in an area away from the biological sample to determine the extent of rinsing.

To minimize effects of photo-bleaching during imaging the images may be acquired at a determined time interval for real-time monitoring. The determined time interval for acquiring the images may be greater than the exposure time. Alternatively or in addition, an anti-fading agent may be added to the biological sample to reduce any photo-bleaching of the sample.

At step 60, at least a portion of the biological sample is destained or bleached. At step 62, while destaining, the sample is monitored to determine an amount of destaining for at least a portion of the biological sample. In one embodiment, the sample may be imaged. The imaging may be used to determine when the biological sample is bleached to a suitable extent.

As the destaining progresses, the optical characteristic, such as light intensity decreases and reaches a minimum value upon completion of destaining. At step 61, data acquired from the biological sample during monitoring is analyzed to evaluate the extent of destaining. For example, data acquired from the images is analyzed to determine the progress in the step of destaining. The data may be analyzed to determine if the light intensity fall off has reached a saturation level. If the desired progress has occurred, the step of destaining may be stopped and the next step of the staining cycle may be started. For example, a new antibody may be introduced in the flow chamber or another biological sample may be provided (step 64). In one example, saturation in intensity falloff may be determined by continuously imaging the sample during the destaining step.

The automated destaining step permits the operator to reprobe a single sample while maintaining the original registration. The addition of the oxidant results in destaining of the biological sample due to substantial removal of the signal produced by the lumiphore. Whether the destaining is accomplished by chemically altering the lumiphore or by detachment, the signal is reduced by at least 80% and preferably greater than 90%. This reduction in signal may be measured as the post-staining intensity at a particular wavelength relative to the initial absolute intensity of the stained biological to adjust for a concomitant reduction in background signal or autofluorescence resulting from the destaining step.

Optionally, prior to destaining, the sample may be imaged to identify a brightest region that needs to be monitored. Next, an initial image may be acquired and brightest region that needs to be monitored may be identified.

In one example, time periods for carrying out each of the steps in the staining cycle may be pre-fed in the system. In this example, the imaging may be carried out to confirm whether the pre-fed time periods are correct. If the time periods for one or more of the steps in the staining cycle are different from the pre-fed time periods, the pre-fed time periods may be updated in the system. These updated time periods may be later used by the system for similar samples in future. In one example, the method may include correlating the light intensity values to a specific labeling of a biomarker.

In some embodiments, a location of the signal in the biological sample may be observed. In some embodiments, a localization of the signal in the biological signal may be observed using morphological stains. In some embodiments relative locations of two or more signals may be observed. A location of the signal may be correlated to a location of the target in the biological sample, providing information regarding localization of different targets in the biological sample. In some embodiments, an intensity value of the signal and a location of the signal may be correlated to obtain information regarding localization of different targets in the biological sample. For examples certain targets may be expressed more in the cytoplasm relative to the nucleus, or vice versa. In some embodiments, information regarding relative localization of targets may be obtained by comparing location and intensity values of two or more signals.

The method of the invention allows minimization of cycle time over complete set of stains/antibodies, thereby improving the through. New stains may be employed using the method of the invention without extensive testing.

The systems and methods disclosed herein may find applications in various fields, such as but not limited to analytic, diagnostic, and therapeutic applications in biology and medicine. In some embodiments, the systems and methods disclosed herein may find applications in histochemistry, particularly, immunohistochemistry. Analysis of cell or tissue samples from a patient, according to the methods described herein, may be employed diagnostically (e.g., to identify patients who have a particular disease, have been exposed to a particular toxin or are responding well to a particular therapeutic or organ transplant) and prognostically (e.g., to identify patients who are likely to develop a particular disease, respond well to a particular therapeutic or be accepting of a particular organ transplant). The methods disclosed herein, may facilitate accurate and reliable analysis of a plurality (e.g., potentially infinite number) of targets (e.g., disease markers) from the same biologically sample.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A closed loop automated method for staining of a biological sample, comprising:
providing a biological sample;
staining at least a portion of the biological sample by flowing in a reagent;
during the staining, monitoring one or more optical characteristics of the biological sample until saturation of at least one of the one or more optical characteristics;
ceasing the reagent flow after saturation of the at least one of the one or more optical characteristics; and
calculating a figure of merit based on at least one of the one or more optical characteristics.

2. The method of claim 1, wherein the figure of merit comprises one or more of a light intensity, a contrast of an image, a Brenner gradient, or a signal to background ratio.

3. The method of claim 1, wherein monitoring comprises acquiring images from the portion of the biological sample during staining.

4. The method of claim 3, comprising closing an illumination shutter when not imaging.

5. The method of claim 1, further comprising adding one or more anti-fading agents to the biological sample to reduce any photo-bleaching of the biological sample.

6. The method of claim 1, further comprising:
destaining at least a portion of the stained portion of the biological sample;
monitoring one or more optical characteristics of the destained portion of the biological sample;
calculating a figure of merit based on at least one of the one or more optical characteristics of the destained portion of the biological sample.

7. The method of claim 6, wherein monitoring comprises acquiring images from the destained portion of the biological sample during destaining.

8. The method of claim 1, further comprising:
rinsing at least a portion of the stained portion of the biological sample; and
monitoring one or more optical characteristics of the rinsed portion of the biological sample; and
calculating a figure of merit based on at least one of the optical characteristics of the rinsed portion of the biological sample.

9. The method of claim 8, wherein monitoring comprises acquiring images from the portion of the biological sample during rinsing.

10. The method of claim 9, further comprising imaging regions away from the rinsed portion of the biological sample.

11. The method of claim 1, further comprising acquiring an initial image of the biological sample prior to staining.

12. The method of claim 11, further comprising rinsing the biological sample with a buffer solution prior to acquiring the initial image.

13. The method of claim 1, further comprising rinsing at least a portion of the biological sample, destaining at least a portion of the biological sample, and wherein monitoring comprises continuously acquiring images during staining, destaining or rinsing.

14. The method of claim 13, comprising real-time monitoring of the biological sample.

15. The method of claim 1, further comprising rinsing at least a portion of the biological sample, destaining at least a portion of the biological sample, and wherein monitoring comprises intermittently acquiring images during staining, destaining or rinsing.

16. The method of claim 15, wherein intermittently acquiring images comprises acquiring images at time intervals greater than an exposure time of the biological sample to an illumination source.

17. The method of claim 1, wherein determining the figure of merit comprises correlating light intensity values with specific labeling of a biomarker.

* * * * *